United States Patent
Fujii et al.

(10) Patent No.: US 8,684,177 B2
(45) Date of Patent: Apr. 1, 2014

(54) STOPPER HOUSING CASE

(75) Inventors: Naoto Fujii, Itabashi-ku (JP); Hirotaka Yoshihara, Itabashi-ku (JP)

(73) Assignee: GC Corporation, Tokyo (JP)

(*) Notice: Subject to any disclaimer, the term of this patent is extended or adjusted under 35 U.S.C. 154(b) by 0 days.

(21) Appl. No.: 13/195,432

(22) Filed: Aug. 1, 2011

(65) Prior Publication Data

US 2012/0028212 A1   Feb. 2, 2012

(30) Foreign Application Priority Data

Aug. 2, 2010  (JP) .................................. 2010-173593

(51) Int. Cl.
*B65D 83/10* (2006.01)

(52) U.S. Cl.
USPC .......................................................... 206/369

(58) Field of Classification Search
USPC .................................. 206/369, 379, 370, 368
See application file for complete search history.

(56) References Cited

U.S. PATENT DOCUMENTS

| | | | | |
|---|---|---|---|---|
| 2,568,089 A * | 9/1951 | Pendleton | ........................ | 211/69 |
| 4,413,731 A * | 11/1983 | Weideman | ..................... | 206/379 |
| 4,619,364 A * | 10/1986 | Czopor, Jr. | ..................... | 206/379 |
| 4,736,843 A * | 4/1988 | Leonard | ......................... | 206/369 |
| 4,811,843 A * | 3/1989 | Stribiak | ......................... | 206/349 |
| 5,692,609 A * | 12/1997 | Lin | ................................. | 206/368 |
| 5,788,488 A | 8/1998 | Grossman | | |
| 5,967,318 A * | 10/1999 | Rosler | ............................ | 206/372 |
| 6,358,049 B1 | 3/2002 | Cerniway | | |
| 6,405,864 B1 | 6/2002 | Streich et al. | | |
| 7,066,329 B2 * | 6/2006 | Riley | ............................. | 206/443 |
| 7,165,674 B2 * | 1/2007 | Pangerc et al. | ............... | 206/379 |
| 2006/0188840 A1 | 8/2006 | Verban, Jr. | | |

FOREIGN PATENT DOCUMENTS

| | | |
|---|---|---|
| DE | 297 20 294 U1 | 12/1998 |
| FR | 2 880 534 A1 | 7/2006 |
| JP | 2003-501135 | 1/2003 |
| WO | WO 00/74585 A2 | 12/2000 |

OTHER PUBLICATIONS

Extended Search Report issued Dec. 5, 2011 in European Patent Application No. 11006236.1-2318.

* cited by examiner

*Primary Examiner* — Jacob K Ackun
(74) *Attorney, Agent, or Firm* — Oblon, Spivak, McClelland, Maier & Neustadt, L.L.P.

(57) ABSTRACT

In a hard material made stopper housing case to house a plurality of cylindrical stoppers for defining a drill blade entering depth of a dental implant fixture embedding hole at a jawbone when performing a dental implant treatment, the stopper has a spring-like locking part to be locked with a flange part projected from a shank part of a drill, the stopper housing case 1 has concave parts 2 provided in parallel and capable of respectively housing the stopper Y, and each of the concave parts 2 includes, at one side, a flange part insertion path 3 having a size preventing the spring-like locking part from falling out and being capable of inserting the flange part, and further includes, at another side opposite to the one side, a drill blade part insertion path 4 capable of inserting the blade part of the drill X.

5 Claims, 3 Drawing Sheets

STOPPER HOUSING CASE

BACKGROUND OF THE INVENTION

1. Field of the Invention

The present invention relates to a stopper housing case capable of housing a plurality of stoppers for defining a drill blade entering depth. The stopper has a cylindrical shape to be fitted on a drill from the blade edge side of a blade part, where the drill is to bore a dental implant fixture embedding hole having a predetermined depth at a jawbone when performing a dental implant treatment. The stopper further has a spring-like locking part to be locked with a flange part projected from a shank part of the drill. In addition, the stopper housing case is capable of easily attaching and detaching the stopper to and from the drill attached to a dental handpiece.

2. Description of the Conventional Art

In recent years, a dental implant treatment has been broadly used as one of dental prosthesis treatments. In the dental implant treatment, a dental implant fixture made of titanium or a titanium alloy having excellent biocompatibility is embedded in a jawbone of a lost tooth part, and is substituted through direct bone bonding (osseointegration) instead of a natural tooth root. Further, the dental implant fixture used in the dental implant treatment is configured separately from an abutment for fixing a dental prosthesis, or is configured integrally with the abutment.

It is necessary for such a dental implant fixture to be embedded into the jawbone to a predetermined depth. Thus, in order to embed the dental implant fixture, conventionally, a stopper for defining the boring depth is attached to the drill for boring the dental implant fixture embedding hole at the jawbone. For attaching the stopper, a method to attach the stopper at a predetermined position of a blade part of the drill with a screw or the like has been used (e.g., refer to Japanese Translation of PCT Application Laid-Open No. 2003-501135). However, since the attachment position must be adjusted at an every attachment operation, it is troublesome. Further, there is a problem that an accident that the stopper is moved could occur if the stopper is not fixed certainly with the screw.

Accordingly, present inventors found out the following. A flange part is provided to project from a shank part of a drill for boring a dental implant fixture embedding hole having a predetermined depth at a jawbone when performing a dental implant fixture treatment. A spring-like locking part provided at a stopper for defining a drill blade entering depth is locked with the flange part. With this configuration, since the flange part is integrated with the shank part of the drill, a problem that an attachment position is moved does not occur unlike the attachment with a screw. So, it is preferable. A drill blade entering depth can be defined easily by providing the flange part integrally with the shank part of the drill, and preparing a plurality of stoppers for defining the drill blade entering depth. The stopper has a cylindrical shape to be fitted on the drill from the blade edge side of a blade part, and has a spring-like locking part to be locked with the flange part projected from the shank part of the drill. However, when the spring-like locking part of the stopper is locked with the flange part projected from the shank part of the drill, the spring-like locking part must be locked with the flange part so as not to be easily detached from the flange part projected from the shank part of the drill. Thus, strong force is necessary for locking the spring-like locking part of the stopper with the flange part projected from the shank part.

SUMMARY OF THE INVENTION

Problems to be Solved by the Invention

An objective of the present invention is to provide a stopper housing case capable of housing a plurality of prepared stoppers and easily attaching and detaching the stoppers to and from a drill attached to a dental handpiece.

Means for Solving the Problem

Present inventors carried out earnest works to solve the aforementioned problems and, as a result, they found out the following stopper housing case to complete the present invention. The stopper housing case for housing a plurality of stoppers for defining a drill blade entering depth is formed with a hard material. The stopper has a cylindrical shape to be fitted on a drill from the blade edge side of a blade part, where the drill is to bore a dental implant fixture embedding hole having a predetermined depth at a jawbone when performing a dental implant treatment. The stopper has a spring-like locking part to be locked with a flange part projected from a shank part of the drill.

The stopper housing case has the following configuration. Concave parts capable of respectively housing the stopper are arranged in parallel. Each of the concave parts includes, at one side, a flange part insertion path having a size preventing the spring-like locking part of the stopper from falling out and capable of inserting the flange part projected from the shank part of the drill. Further, each of the concave parts includes, at another side opposite to the one side, a drill blade part insertion path capable of inserting the blade part of the drill. According to this configuration, since the stoppers can be attached and detached in the stopper housing case, the stoppers are not lost. In addition, the stoppers for defining a desired drill blade entering depth can be found easily.

More specifically, according to an aspect of the present invention, a stopper housing case is formed with a hard material to house a plurality of stoppers for defining a drill blade entering depth. The stopper has a cylindrical shape to be fitted on a drill from the blade edge side of a blade part, where the drill is to bore a dental implant fixture embedding hole having a predetermined depth at a jawbone when performing a dental implant treatment. The stopper has a spring-like locking part to be locked with a flange part projected from a shank part of the drill.

In the stopper housing case, concave parts capable of respectively housing the stoppers are arranged in parallel. Each of the concave parts includes, at one side, a flange part insertion path having a size preventing the spring-like locking part of the stopper from falling out and capable of inserting the flange part projected from the shank part of the drill. Further, each of the concave parts includes, at another side opposite to the one side, a drill blade part insertion path capable of inserting the blade part of the drill.

Furthermore, in the stopper housing case having the aforementioned configuration, when end parts at the drill blade part insertion path side of the concave parts are provided so as to align together, the flange part insertion path side of the stopper housing case comes to be in a projecting state corresponding to the lengths of the stoppers. Since the stopper can be thus selected easily, it is preferable. When projections to be engaged with a concave groove formed on an outer peripheral face of the stopper are provided on an inner face of the flange part insertion path in the concave part, the stopper can be housed stably in the stopper housing case. In addition, at a time of attaching and detaching the stopper, the projections are engaged with the concave groove formed on the outer peripheral face of the stopper, the stopper is not loosened, and it is preferable. Furthermore, when the stopper housing case further includes slide guide parts and a cap, the stoppers can be stably stored in the stopper housing case without falling out of the stopper housing case at a time of not using the stoppers, so that it is preferable. The slide guide parts are provided on both side faces in parallel with the drill blade part insertion paths in the stopper housing case. The cap includes guide parts provided on both side parts of an inner face of the cap along the slide guide parts to slide-engage with the slide guide parts. With this configuration, the cap prevent the stoppers housed in the concave parts from falling out of the concave part.

Effect of the Invention

A stopper housing case according to the present invention is formed with a hard material for housing a plurality of stoppers for defining a drill blade entering depth. The stopper has a cylindrical shape to be fitted on a drill from the blade edge side of a blade part, where the drill is to bore a dental implant fixture embedding hole having a predetermined depth at a jawbone when performing a dental implant treatment. The stopper has the spring-like locking part to be locked with a flange part projected from a shank part of the drill. The concave parts capable of respectively housing the stoppers are arranged in parallel. Each of the concave parts includes, at one side, a flange part insertion path having a size preventing the spring-like locking part of the stopper from falling out and capable of inserting the flange part projected from the shank part of the drill. Further, each of the concave parts includes, at another side opposite to the one side, the drill blade part insertion path capable of inserting the blade part of the drill. According to this configuration, when the stopper is mounted on the drill attached to the dental handpiece, the drill attached to the dental handpiece is moved toward the stopper, which is housed in the concave part so as to position the spring-like locking part at the flange part insertion path side. The blade part of the drill is inserted into a through hole penetrating the stopper so as to pass through, and a top end of the blade part of the drill is positioned in the drill blade part insertion path. While keeping this state, the flange part projected from the shank part of the drill is made to pass through the flange part insertion path, and pushed into and locked with the spring-like locking part of the stopper. Then, the drill is pulled out upward from the concave part, the drill blade part insertion path, and the flange part insertion path. On the other hand, when the stopper is taken out from the drill attached to the dental handpiece, the drill is inserted from upside so as to respectively position the blade part of the drill in the drill blade part insertion path, the spring-like locking part of the stopper in the concave part so as to position it at the flange part insertion path side, and the shank part of the drill in the flange part insertion path. Then, the dental handpiece is moved in the direction of separating from the flange part insertion path. At this time, the spring-like locking part of the stopper cannot move, because the spring-like locking part of the stopper contacts to the opposite side to the drill blade part insertion path of the flange part insertion path. Thus, the flange part projected from the shank part of the drill comes out from the inside of the spring-like locking part of the stopper, and passes through the flange part insertion path, so that only the stopper remains in the concave part and can be taken out of the drill attached to the dental handpiece.

Accordingly, since the stopper can be attached and detached in the stopper housing case, the stopper is not lost, and the stopper for defining a desired drill blade entering depth can be found easily.

Furthermore, when end parts at the drill blade part insertion path side of the concave parts are provided so as to align together, the flange part insertion path side of the stopper housing case comes to be in a projecting state corresponding to the lengths of the stoppers. Since the stopper can be thus selected easily, it is preferable. When projections to be engaged with a concave groove formed on an outer peripheral face of the stopper are provided on an inner face of the flange part insertion path of the concave part, the stopper can be housed stably in the stopper housing case. In addition, at a time of attaching and detaching the stopper, the projections are engaged with the concave groove formed on the outer peripheral face of the stopper, the stopper is not loosened, and it is preferable. Furthermore, when the stopper housing case further includes slide guide parts and a cap, the stoppers can be stably housed in the stopper housing case without falling out of the stopper housing case at a time of not using the stoppers, so that it is preferable. The slide guide parts are provided on both side faces in parallel with the drill blade part insertion path in the stopper housing case. The cap includes guide parts provided on both side parts of an inner face of the cap along the slide guide parts to slide-engage with the slide guide parts. With this configuration, the cap can prevent the stoppers housed in the concave parts from falling out of the concave part.

DETAILED DESCRIPTION OF PREFERRED EMBODIMENT

Figure 1:
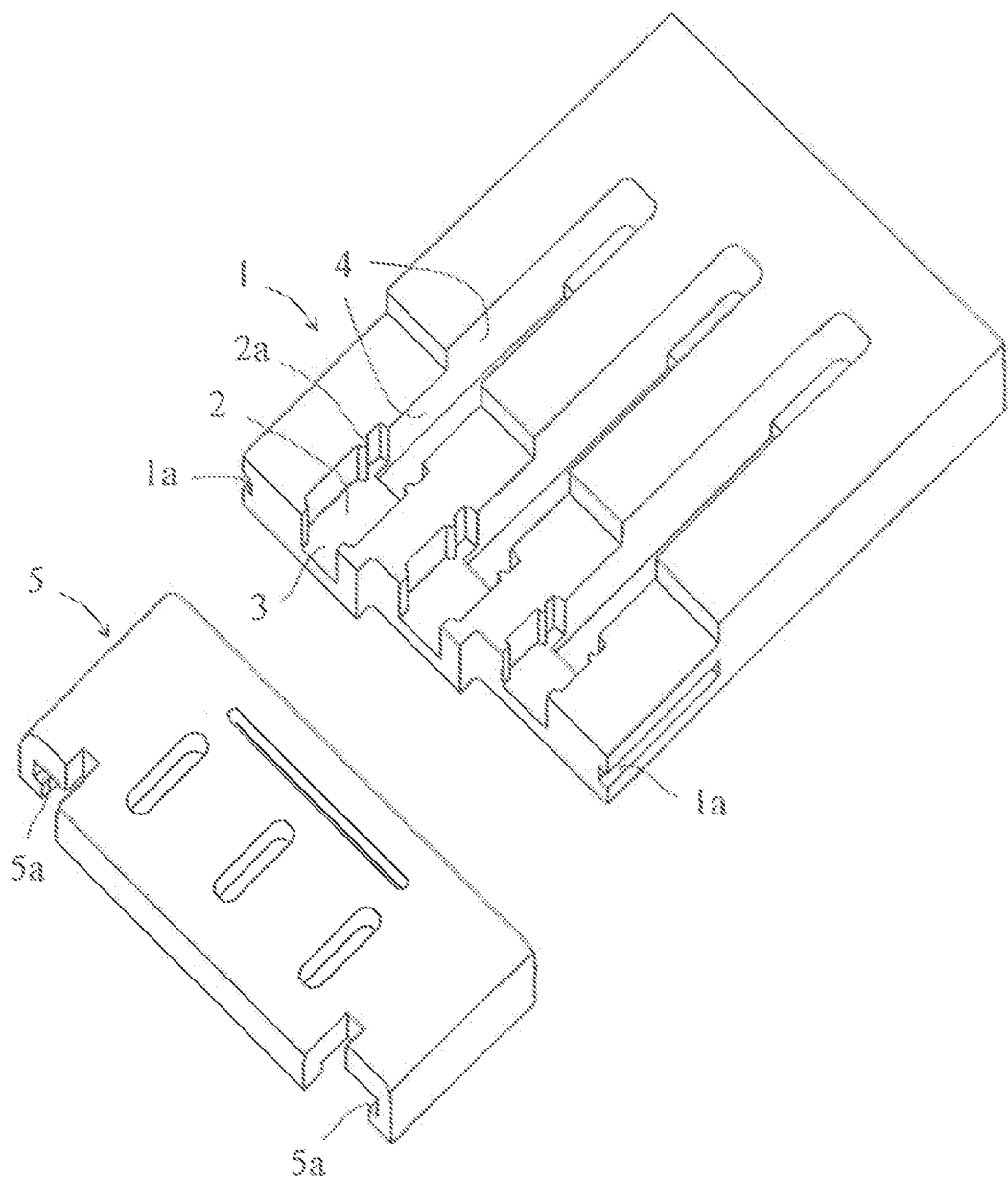
FIG. 1 is a perspective view illustrating an exemplary embodiment of a stopper housing case according to the present invention.
Figure 2:
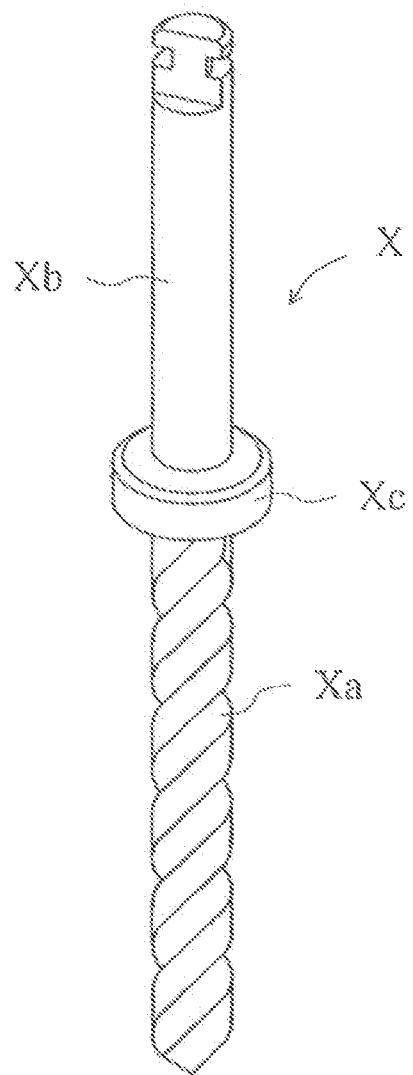
FIG. 2 is a perspective explanatory view illustrating an example of a drill having a flange part, which is projected from a shank part, to bore a dental implant fixture embedding hole at a jawbone when performing a dental implant treatment.
Figure 3:
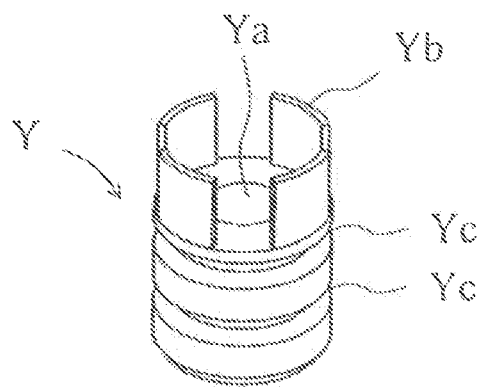
FIG. 3 is a perspective view illustrating an example of a stopper for defining a drill blade entering depth, where the stopper is fitted on the drill illustrated in FIG. 2 from the blade edge side of a blade part, and has a spring-like locking part to be locked with the flange part projected from the shank part of the drill.
Figure 4:
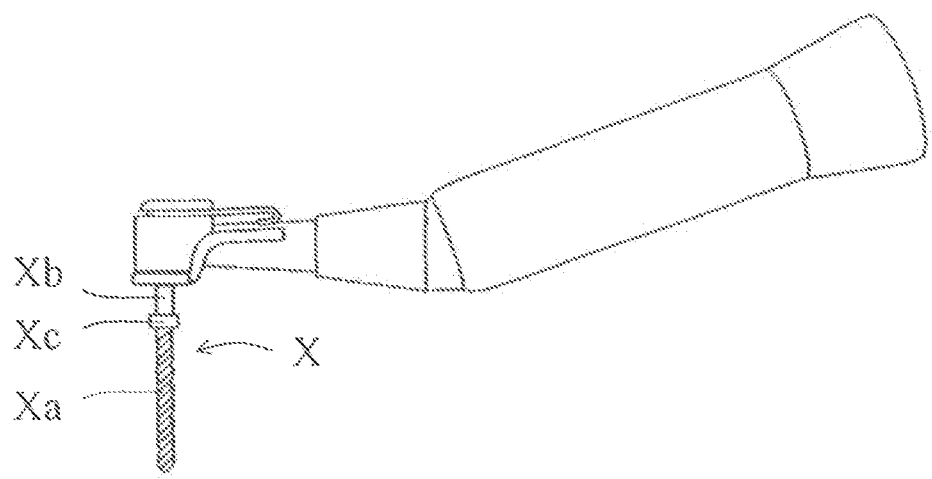
FIG. 4 is a perspective view illustrating a state that the drill illustrated in FIG. 2 on which the stopper illustrated in FIG. 3 is mounted is attached to a dental handpiece.
Figure 5:
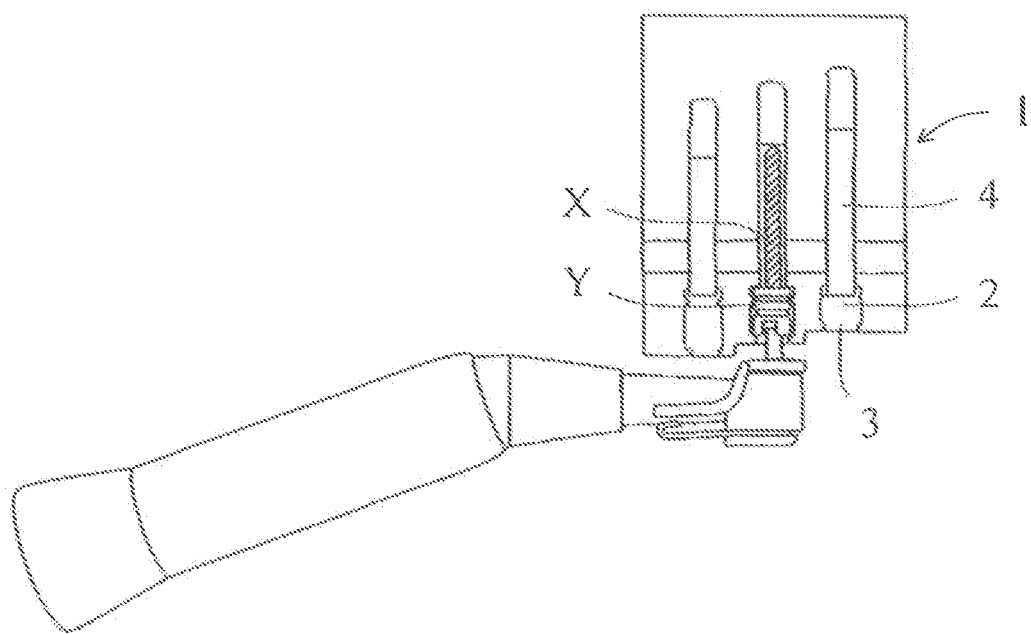
FIG. 5 is a perspective view illustrating a state that the dental handpiece illustrated in FIG. 4 to which the drill mounted with the stopper is attached is positioned at a predetermined position of a stopper housing case according to the present invention.

In the drawings, a drill X includes a blade part Xa for boring a dental implant fixture embedding hole at a jawbone when performing a dental implant treatment. A flange part Xc is projected from a shank part Xb.

A stopper Y for defining a drill blade entering depth has a cylindrical shape having a through hole Ya into which the drill X is inserted from the blade edge side of the blade part Xa. The stopper Y has a spring-like locking part Yb to be locked with the flange part Xc projected from the shank part Xb.

When the spring-like locking part Xb is locked with the flange part Xc of the drill X, the spring-like locking part Yb needs to expand once and then return to an original state by its spring action. Thus, a few slits are provided in parallel with the through hole Ya. Furthermore, it is preferable that concave grooves Yc are peripherally provided for every predetermined length on an outer periphery of the cylindrical part following the spring-like locking part Yb.

A stopper housing case 1 according to the present invention is formed with a hard material such as a metal, hard plastic, or the like. In the stopper housing case 1, concave parts 2 capable of respectively housing the stoppers Y are provided in parallel. The concave part 2 includes a flange part insertion path 3 formed at one side. The flange part insertion path 3 has a size preventing the spring-like locking part Yb of the stopper Y from falling out, and capable of inserting the flange part Xc projected from the shank part Xb of the drill X. Further, the concave part 2 includes a drill blade part insertion path 4 formed at another side opposite to the one side. The drill blade part insertion path 4 is capable of inserting the blade part Xa of the drill X.

A cap 5 is preferably provided on the stopper housing case 1 according to the present invention. The cap 5 functions for preventing the stoppers Y housed in the concave parts 2 from falling out of the concave parts 2 by slide-engaging of guide parts 5a with slide guide parts 1a. The slide guide parts 1a are provided on both side faces in parallel with the drill blade part insertion path 4 of the stopper housing case 1. The guide parts 5a are provided on side parts of an inner face of the cap along the slide guide parts 1a.

In the configuration mentioned above, when end parts at the drill blade part insertion path 4 side of the concave parts 2 are provided so as to align together, the flange part insertion path 3 side of the stopper housing case 1 comes to be in a projecting state corresponding to the lengths of the stoppers Y. Since the stopper Y can be thus selected easily, it is preferable. When projection 2a to be engaged with a concave groove Yc formed on an outer peripheral face of the stopper Y are provided on an inner face of the flange part insertion path of the concave part 2, the stoppers Y can be housed stably in the stopper housing case 1. In addition, at a time of attaching and detaching the stopper Y, the projections are engaged with concave groove Yc formed on the outer peripheral face of the stopper Y, and the stopper Y is not loosened, so it is preferable. When the stopper housing case 1 further includes slide guide parts 1a and the cap 5, the stoppers Y can be stably housed in the stopper housing case 1 without falling out of the stopper housing case 1 at a time of not using the stoppers Y, so that it is preferable. The slide guide parts 1a are provided on both side faces in parallel with the drill blade part insertion path 4 in the stopper housing case 1. The guide parts 5a provided in the cap 5 along the slide guide parts 1a slide-engage with the slide guide part 1a. With this configuration, the cap 5 can prevent the stoppers Y housed in the concave parts 2 from falling out of the concave part 2.

When the stopper Y is mounted on the drill X attached to a dental handpiece by using the stopper housing case 1 according to the present invention, the drill X attached to the dental handpiece is moved toward the stopper Y, which is housed in the concave part 2 so as to position the spring-like locking part Yb at the flange part insertion path 3 side. The blade part Xa of the drill X is inserted into the through hole Ya penetrating the stopper Y so as to pass through, and a top end of the blade part Xa of the drill X is positioned in the drill blade part insertion path 4. While keeping this state, the flange part Xc projected from the shank part Xb of the drill X is made to pass through the flange part insertion path 3, and pushed into and locked with the spring-like locking part Yb of the stopper Y. Then, the drill X is pulled out upward from the concave part 2, the drill blade part insertion path 4, and the flange part insertion path 3.

On the other hand, when the stopper Y is taken out from the drill X attached to the dental handpiece by using the stopper housing case 1 according to the present invention, the drill X is inserted from upside so as to respectively position the blade part Xa of the drill X in the drill blade insertion path 4, the spring-like locking part Yb of the stopper Y in the concave part 2 so as to position it at the flange part insertion path 3 side, and the shank part Xb of the drill X in the flange part insertion path 3. Then, the dental handpiece is moved in the direction of separating from the flange part insertion path 3. At this time, the spring-like locking part Yb of the stopper Y cannot move because the spring-like locking part Yb of the stopper Y contacts to the opposite side to the drill blade part insertion path 4 of the flange part insertion path 3. Thus, the flange part Xc projected from the shank part Xb of the drill X comes out from the inside of the spring-like locking part Yb of the stopper Y, and passes through the flange part insertion path 3. Thus, only the stopper Y remains in the concave part 2, so that the stopper Y can be taken out of the drill X attached to the dental handpiece.

Furthermore, when the stoppers Y are not used, the stoppers Y are housed in the concave part 2 in the stopper housing case 1 according to the present invention so as to position the spring-like locking parts Yb at the flange part insertion path 3 side. However, when the stopper housing case 1 further includes slide guide parts 1a and a cap 5, the stoppers Y can be stably housed in the stopper housing case 1 without falling out of the stopper housing case 1 at a time of not using the stoppers Y, so that it is preferable. The slide guide parts 1a are provided on both side faces in parallel with the drill blade part insertion paths 4 in the stopper housing case 1. The guide parts 5a provided on both side parts of an inner face of the cap 5 along the slide guide parts 1a to slide-engage with the slide guide parts 1a. With this configuration, the cap 5 can prevent the stoppers Y housed in the concave parts 2 from falling out of the concave parts 2.

What is claimed is:

1. A stopper housing case for housing cylindrical stoppers that each fit from a blade edge side of a blade part of a drill for boring a dental implant fixture embedding hole at a jawbone, thereby defining a drill blade entering depth of the blade part of the drill, the stoppers each locking, via a spring-like locking part, to a flange part projected from a shank part of the drill, said case comprising:
   concave parts in parallel to one another, each capable of housing one of the stoppers,
   a flange part insertion path at one side of each concave part,
   a projection on an inner face of each flange part insertion path configured to engage with a concave groove on an outer peripheral face of a stopper,
   a drill blade part insertion path at a side of each of the concave parts opposite to the one side, the insertion path capable of housing the blade part of the drill,
   slide guide parts on side faces of the stopper housing case in parallel with the drill blade part insertion paths, and
   a cap configured to slide-engage with the slide guide parts and prevent the stoppers from falling out of the concave parts, the cap comprising guide parts on side parts of an inner face of the cap,
   wherein the stopper housing case comprises a hard plastic.

2. The stopper housing case of claim 1, wherein end parts of each drill blade part insertion path side of the concave parts align together.

3. A stopper apparatus, comprising:

cylindrical stoppers, each configured to fit from a blade edge side of a blade part of a drill for boring a dental implant fixture embedding hole at a jawbone, thereby defining a drill blade entering depth of the blade part of the drill, and a hard plastic stopper housing case for housing the stoppers, wherein the case comprises concave parts in parallel to one another, each capable of housing one of the stoppers; a flange part insertion path at one side of each concave part; a projection on an inner face of each flange part insertion path; and a drill blade part insertion path at a side of each of the concave parts opposite to the one side, the insertion path capable of housing the blade part of the drill, and wherein each stopper in the plurality of stoppers comprises a spring-like locking part configured to lock with a flange part projected from a shank part of a drill; and a concave groove configured to engage with the projection on the inner face of the flange part insertion path of the stopper housing case.

4. The stopper apparatus of claim 3, wherein the hard plastic stopper housing case further comprises:

slide guide parts on side faces of the stopper housing case in parallel with the drill blade part insertion paths, and a cap configured to slide-engage with the slide guide parts and prevent the stoppers from falling out of the concave parts, the cap comprising guide parts on side parts of an inner face of the cap.

5. The stopper apparatus of claim 3, wherein end parts of each drill blade part insertion path side of the concave parts align together.

\* \* \* \* \*